(12) United States Patent
Green et al.

(10) Patent No.: US 10,446,385 B2
(45) Date of Patent: Oct. 15, 2019

(54) METHOD OF SEPARATING IONS

(71) Applicant: Micromass UK Limited, Wilmslow (GB)

(72) Inventors: Martin Raymond Green, Bowdon (GB); Kevin Giles, Stockport (GB); David John Langridge, Macclesfield (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/596,451

(22) Filed: May 16, 2017

(65) Prior Publication Data

US 2017/0338093 A1 Nov. 23, 2017

(30) Foreign Application Priority Data

May 17, 2016 (GB) .................... 1608653.0

(51) Int. Cl.
*H01J 49/00* (2006.01)
*H01J 49/40* (2006.01)
*G01N 27/62* (2006.01)
*G01N 30/02* (2006.01)
*G01N 30/58* (2006.01)

(52) U.S. Cl.
CPC ............ *H01J 49/40* (2013.01); *G01N 27/622* (2013.01); *G01N 2030/025* (2013.01); *G01N 2030/027* (2013.01); *G01N 2030/582* (2013.01)

(58) Field of Classification Search
CPC .. H01J 49/00; H01J 49/02; H01J 49/06; H01J 49/062; H01J 49/063; H01J 49/065; H01J 49/0655
USPC ........ 250/281, 282, 283, 290, 291, 292, 293
See application file for complete search history.

(56) References Cited

U.S. PATENT DOCUMENTS

| | | | |
|---|---|---|---|
| 6,124,592 A | 9/2000 | Spangler | |
| 7,268,347 B1 | 9/2007 | Blanchard | |
| 7,838,826 B1 | 11/2010 | Park | |
| 9,466,473 B2 | 10/2016 | Giles et al. | |
| 9,683,964 B2 | 6/2017 | Park et al. | |
| 2003/0141446 A1 | 7/2003 | Blanchard | |

(Continued)

FOREIGN PATENT DOCUMENTS

EP 3054473 A1 8/2016
WO 1999/47912 A1 9/1999

(Continued)

OTHER PUBLICATIONS

Combined Search and Examination Report for GB Application No. GB1707918.7 dated Oct. 30, 2017.

(Continued)

*Primary Examiner* — Jason L McCormack

(57) ABSTRACT

The present disclosure relates generally to a method of separating ions according to their ion mobility, comprising (i) accumulating a first population of ions in a first region of an ion mobility separator, (ii) separating said first population of ions according to their ion mobility in said first region of said ion mobility separator, and (iii) accumulating a second population of ions in said first region of said ion mobility separator while said first population of ions are being separated according to their ion mobility in said ion mobility separator.

20 Claims, 2 Drawing Sheets

(56) References Cited

U.S. PATENT DOCUMENTS

| | | | | |
|---|---|---|---|---|
| 2011/0095175 A1* | 4/2011 | Bateman | .............. | G01N 27/624 |
| | | | | 250/282 |
| 2012/0256083 A1* | 10/2012 | Kovtoun | ............... | H01J 49/004 |
| | | | | 250/282 |
| 2015/0340221 A1* | 11/2015 | Benner | .................. | H01J 49/22 |
| | | | | 250/282 |
| 2017/0117129 A1* | 4/2017 | Pringle | ................ | G01N 27/622 |

FOREIGN PATENT DOCUMENTS

| | | | | |
|---|---|---|---|---|
| WO | 2014/140579 A1 | 9/2014 | | |
| WO | WO 2014174260 A1 * | 10/2014 | ........... | G01N 27/622 |
| WO | WO-2014174260 A1 * | 10/2014 | ........... | G01N 27/622 |

OTHER PUBLICATIONS

Extended European Search Report for EP Application No. 17171566.7 dated Oct. 5, 2017.

* cited by examiner

METHOD OF SEPARATING IONS

CROSS-REFERENCE TO RELATED APPLICATION

This application claims priority from and the benefit of United Kingdom patent application no. 1608653.0, filed on 17 May 2016. The entire content of this application is incorporated by reference.

FIELD OF THE INVENTION

The present invention relates generally to methods of separating ions, for example according to mass or ion mobility, and ion separators such as ion mobility separators or mass separators.

BACKGROUND

A single ion trap may be used upstream of an ion mobility separator in order to improve the duty cycle when transferring successive populations of ions into the ion mobility separator. Application of relatively high voltage extraction field is typically required to ensure rapid transfer of ions from the ion trap to the ion mobility separator with minimal dispersion. Application of such a high voltage field can cause heating of the ions, resulting in undesired fragmentation (e.g., of labile compounds). However, slower transfer of ions from the ion trap can lead to a lower duty cycle.

In addition, the ion cloud may not be driven far enough into the ion mobility separator, and may not experience the desired ion mobility separation force during subsequent operation. In this case ions can be lost or remain trapped at the front region of the ion mobility separator.

US2003/0141446 (Blanchard) discloses an ion detecting apparatus and methods.

WO 99/47912 (Spangler) discloses an ion mobility storage trap and method.

U.S. Pat. No. 7,838,826 (Park) discloses an apparatus and method for parallel flow ion mobility spectrometry combined with mass spectrometry.

WO 2014/140579 (Micromass) discloses a coaxial ion guide.

It is desired to provide an improved method of separating ions according to their ion mobility.

SUMMARY

According to an aspect of the present disclosure there is provided a method of separating ions according to their ion mobility, comprising:

(i) accumulating a first or preceding population of ions in a first region of an ion mobility separator;

(ii) separating the first or preceding population of ions according to their ion mobility in the first region of the ion mobility separator; and (iii) accumulating a second or subsequent population of ions in the first region of the ion mobility separator whilst the first or preceding population of ions are being separated according to their ion mobility in the ion mobility separator.

The above method provides a first region of an ion mobility separator that acts as both an accumulation region and an ion mobility separation region. Successive populations of ions may be accumulated in the first region and then separated according to their ion mobility in the first region. This avoids having to rapidly transfer successive populations of ions from an accumulation region (e.g., an external ion trap) into the ion mobility separator to be separated, as they are already present within it.

Conventional arrangements, for example those described in US2003/0141446 (Blanchard), do not disclose an accumulation region that is also used as an ion mobility separation region.

The separation of the first population of ions may not be limited to the first region. As discussed herein, the ion mobility separation region may include the first region, as well as further ion mobility separation regions downstream thereof.

In various embodiments the first region may act in a trapping mode during step (i) and then switch to an ion mobility separation mode in step (ii). The switching may be instantaneous or substantially instantaneous.

Step (ii) may comprise accumulating the second population of ions in an accumulation region upstream of the first region, whilst the first population of ions are being separated according to their ion mobility in the ion mobility separator (e.g., in the first region). The upstream accumulation region may be or form part of an ion trap, for example an ion trap external to the ion mobility separator.

The use of two accumulation regions has been found to improve upon arrangements that involve only a single accumulation region, for example where an accumulating ion trap is located upstream of an ion mobility separator. This avoids, for example, transferring ions into the ion mobility separator (or ion mobility separation region) suddenly, which can lead to ion losses and/or fragmentation.

Step (iii) may comprise transferring the second population of ions from the upstream accumulation region to the first region. Step (iii) may further comprise continuing to pass ions through the upstream accumulation region and into the first region, for example to add to and/or increase the number of ions in the second population of ions (now accumulating in the first region).

The ion mobility separator may comprise a second region downstream of the first region, and step (ii) may comprise separating the first population of ions according to their ion mobility in the first and second regions of the ion mobility separator. Upon initiation of step (ii), the first population of ions may all be located within the first region, and a driving force may be applied to drive the first population of ions along the ion mobility separation region of the ion mobility spectrometer (which may comprise the first and second regions).

Step (iii) may comprise accumulating the second population of ions in the first region of the ion mobility separator whilst the first population of ions are being separated according to their ion mobility in the second region of the ion mobility separator.

Step (iii) may comprise accumulating the second population of ions in the first region of the ion mobility separator after the first population of ions have exited the first region of the ion mobility separator.

The method may further comprise:

(iv) separating the second population of ions according to their ion mobility in the ion mobility separator; and (v) accumulating a third population of ions in the first region of the ion mobility separator whilst the second population of ions are being separated according to their ion mobility.

An incoming beam of ions, for example a continuous beam of ions, may be directed towards the upstream accumulation region.

Taking the second population of ions as an example, this population may begin to accumulate in the upstream accumulation region with ions from the incoming beam of ions.

Once the first population of ions has left the first region of the ion mobility separator, the ions within the upstream accumulation region (i.e., the second population of ions at that point) are transferred to the first region. This period may be relatively slow to avoid ion heating and undesired fragmentation.

During this period ions from the incoming beam of ions may continue to enter the upstream accumulation region and pass through to the first region, adding to and increasing the number of ions in the second population of ions, which is now accumulating in the first region of the ion mobility separator.

It will be appreciated that, throughout this cycle, ions from the incoming beam of ions may either accumulate in the upstream accumulation region, or pass through this region and accumulate in the first region of the ion mobility separator. This can mean that no ions from the incoming beam of ions are lost to the system or otherwise, and a 100% duty cycle can be achieved.

The method may further comprise:

repeating steps (ii) to (v) for the third and further populations of ions, such that subsequent populations of ions are accumulated in the first region of the ion mobility separator whilst preceding populations of ions are being separated according to their ion mobility.

Step (v) may comprise accumulating the third population of ions in the upstream accumulation region whilst the second population of ions are being separated according to their ion mobility in the ion mobility separator.

Step (iv) may comprise separating the second population of ions according to their ion mobility in the first region of the ion mobility separator, or step (iv) may comprise separating the second population of ions according to their ion mobility in the first and second regions of the ion mobility separator.

Step (v) may comprise accumulating the third population of ions in the first region of the ion mobility separator whilst the second population of ions are being separated according to their ion mobility in the second region of the ion mobility separator.

Step (v) may comprise accumulating the third population of ions in the first region of the ion mobility separator after the second population of ions have exited the first region of the ion mobility separator.

Any or all of the steps (i) to (v) may occur sequentially in time.

During a first time period $T_0$-$T_1$ the first population of ions may be accumulated in the first region.

During a second time period $T_1$-$T_2$ the first population of ions may be separated according to their ion mobility (e.g., in the ion mobility separation region of the ion mobility separator, which may comprise the first region and the second region), and the second population of ions may be accumulating in the upstream accumulation region.

During a third time period $T_2$-$T_3$ the first population of ions may have exited the first region, but may not have exited the second region, and the second population of ions may now be transferred to and begin accumulating in the first region. The second population of ions may include ions that enter and are passed through the upstream accumulation region and reach the first region of the ion mobility separator during this period.

During a fourth time period $T_3$-$T_4$, the second population of ions may finish accumulating in the first region, and may be separated according to their ion mobility (e.g., in the ion mobility separation region), and the third population of ions may be accumulating in the upstream accumulation region. The first population of ions may have exited the ion mobility separator or ion mobility separation region.

During a fifth time period $T_4$-$T_5$, the second population of ions may have exited the first region, but may not have exited the second region, and the third population of ions may now be transferred to and begin accumulating in the first region. The third population of ions may include ions that enter and are passed through the upstream accumulation region and reach the first region of the ion mobility separator during this period.

During a sixth time period $T_5$-$T_6$, the third population of ions may be separated according to their ion mobility (e.g., in the ion mobility separation region), and a further population of ions may be accumulated in the upstream accumulation region. The second population of ions may have exited the ion mobility separator or ion mobility separation region.

It will be appreciated that this cycle could continue for further populations of ions.

The ion mobility separator may comprise an RF-confined ion mobility separator.

The ion mobility separator may comprise a plurality of electrodes or axial groups of electrodes stacked adjacent to one another, wherein alternate phases of an RF voltage are applied to adjacent electrodes or electrodes within the axial groups of electrodes.

Each of the plurality of electrodes may comprise apertures through which ions travel in use.

The plurality of electrodes may comprise a plurality of pairs of electrodes stacked adjacent to one another, wherein alternate phases of an RF voltage are applied to adjacent pairs of electrodes.

Each pair of electrodes may comprise a first plate electrode opposite a second plate electrode, wherein in use ions travel through the gap between the first and second plate electrodes.

The first region and/or the second region of the ion mobility separator may comprise RF-confined regions of the ion mobility separator. The ion mobility separator may comprise a longitudinal stack of electrodes, or axial groups of electrodes, and the first region and/or the second region may comprise portions or sections of said longitudinal stack of electrodes, or axial groups of electrodes.

The ion mobility separator may be located within a single region or vacuum region, for example of a mass or ion mobility spectrometer.

The first region of the ion mobility separator may be arranged and adapted to switch between a trapping mode, in which ions are substantially trapped within the first region, and an ion mobility separation mode, in which ions are separated according to their ion mobility within the first region.

The upstream accumulation region may be arranged and adapted to trap or accumulate a population of ions and then transfer the population of ions from the sec upstream accumulation region into the first region.

The upstream accumulation region may be arranged and adapted to switch between a trapping mode, in which ions are substantially trapped within the upstream accumulation region, and an ion guiding mode, in which ions are passed from and/or through the upstream accumulation region into the first region.

The upstream accumulation region may comprise RF-confined regions of an ion trap. The ion trap may comprise a longitudinal stack of electrodes, or axial groups of electrodes, and the upstream accumulation region may comprise portions or sections of said longitudinal stack of electrodes, or axial groups of electrodes.

The populations of ions, for example any of the first, second or third populations of ions, may be accumulated in the first region such that within the first region the first population of ions has a relatively small spatial spread in the direction of ion mobility separation, and a relatively large spatial spread in the direction orthogonal to ion mobility separation. The direction of ion mobility separation may be defined as the direction of ion movement when ions are separated according to their ion mobility within the ion mobility separator, for example during steps (ii) and/or (iv).

A control system of the ion mobility separator may be arranged and adapted to cause ions to accumulate in the first region such that, within the first region, ions have a relatively small spatial spread in the direction of ion mobility separation, and a relatively large spatial spread in the direction orthogonal to ion mobility separation, for example immediately prior to the ions being separated according to their ion mobility.

In various embodiments the method may instead be a method of separating ions according to mass or mass to charge ratio, and the ion mobility separator may instead be a mass separation device, for example a high-pressure mass separation device. The features described above in relation to the ion mobility separator, for example the arrangement of electrodes and/or the voltages applied thereto, may also be features of the mass separation device. The method features relating to the first, second and accumulation regions may be applied mutatis mutandis to a mass separation device comprising these regions and arranged in the same manner as the ion mobility separator described above. For example, in such embodiments the first region may be arranged and adapted to switch between a trapping mode, in which ions are substantially trapped within the first region, and a separation mode, in which ions are separated according to mass or mass to charge ratio within the first region.

According to an aspect of the present disclosure there is provided an ion mobility separator comprising a first region arranged and adapted to accumulate consecutive populations of ions, and a control system arranged and adapted:

(i) to accumulate a first or preceding population of ions in the first region of the ion mobility separator;

(ii) to separate the first or preceding population of ions according to their ion mobility in the first region of the ion mobility separator; and (iii) to accumulate a second or subsequent population of ions in the first region of the ion mobility separator whilst the first or preceding population of ions are being separated according to their ion mobility in the ion mobility separator.

According to an aspect of the present disclosure there is provided a method of separating ions in a device, for example an ion mobility separation device, wherein the device comprises a first region, an accumulation region upstream of the first region and a second region downstream of the first region, and the method comprises the steps of:

(i) driving a first population of ions through the first and second regions so as to separate a first population of ions, for example according to their ion mobility, whilst accumulating a second population of ions in the accumulation region;

(ii) after the first population of ions has exited the first region, but prior to the first population of ions exiting the second region, transferring the second population of ions into the first region and trapping the second population of ions within the first region; and then (iii) driving the second population of ions through the first and second regions so as to separate the second population of ions, for example according to their ion mobility, whilst accumulating a third population of ions in the accumulation region; and optionally (iv) repeating steps (ii) and (iii) for the third and further populations of ions so as to successively separate the third and further populations of ions, for example according to their ion mobility.

The device may comprise a device for separating ions according to their mass or mass to charge ratio, for example a high-pressure mass separation device, or a device for separating ions according to their ion mobility, for example an ion mobility spectrometer.

The first and second regions and/or the accumulation region may comprise RF-confined regions, for example an RF-confined regions of a mass separation device or an ion mobility separator.

The first and second regions and/or the accumulation region may comprise a plurality of electrodes or axial groups of electrodes stacked adjacent to one another, wherein alternate phases of an RF voltage are applied to adjacent electrodes or electrodes within the axial groups of electrodes.

Each of the plurality of electrodes may comprise apertures through which ions travel in use.

The plurality of electrodes may comprise a plurality of pairs of electrodes stacked adjacent to one another, wherein alternate phases of an RF voltage are applied to adjacent pairs of electrodes.

Each pair of electrodes may comprise a first plate electrode opposite a second plate electrode, wherein in use ions travel through the gap between the first and second plate electrodes.

The first region and/or the second region of the device may comprise RF-confined regions of the device. The device may comprise a longitudinal stack of electrodes, or axial groups of electrodes, and the first region and/or the second region and/or the accumulation region may comprise portions or sections of said longitudinal stack of electrodes, or axial groups of electrodes.

The first region of the device may be arranged and adapted to switch between a trapping mode, in which ions are substantially trapped within the first region, and a separation mode, in which ions are separated, for example according to their mass, mass to charge ratio or ion mobility within the first region.

The accumulation region of the device may be arranged and adapted to trap or accumulate a population of ions and then transfer the population of ions from the accumulation region into the first region.

The accumulation region of the device may be arranged and adapted to switch between a trapping mode, in which ions are substantially trapped within the accumulation region, and an ion guiding mode, in which ions are passed from and/or through the accumulation region into the first region.

According to an aspect of the present disclosure there is provided an apparatus comprising a device for separating ions, for example an ion mobility separation device, and a control system, wherein the device comprises a first region, an accumulation region upstream of the first region and a second region downstream of the first region, and the control system is arranged and adapted:

(i) to drive a first population of ions through the first and second regions so as to separate the first population of ions, for example according to their ion mobility, whilst accumulating a second population of ions in the accumulation region;

(ii) after the first population of ions has exited the first region, but prior to the first population of ions exiting the second region, to transfer the second population of ions into the first region and trap the second population of ions within the first region; and then (iii) to drive the second population of ions through the first and second regions so as to separate the second population of ions, for example according to their ion mobility, whilst accumulating a third population of ions in the accumulation region; and optionally (iv) to repeat steps (ii) and (iii) for the third and further populations of ions so as to successively separate the third and further populations of ions, for example according to their ion mobility.

According to an aspect of the present disclosure there is provided an ion mobility separation device, for example a high duty cycle ion mobility separation device, the device comprising:

an RF confined ion mobility separation region;

a first ion trapping region upstream of said ion mobility separation region; and a second ion trapping region upstream of said first ion trapping region;

wherein in operation:

ions are accumulated in said first trapping region for a first portion of an ion mobility separation cycle time $T_1$-$T_2$; and ions are accumulated in said second trapping region for a second portion of an ion mobility separation cycle time $T_3$-$T_4$.

The first trapping region may form part of the ion mobility separation region for part of the ion mobility separation cycle.

The spectrometer may comprise an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; (xxviii) a Laser Ablation Electrospray Ionisation ("LAESI") ion source; and (xxix) Surface Assisted Laser Desorption Ionisation ("SALDI").

The spectrometer may comprise one or more continuous or pulsed ion sources.

The spectrometer may comprise one or more ion guides.

The spectrometer may comprise one or more ion mobility separation devices and/or one or more Field Asymmetric Ion Mobility Spectrometer devices.

The spectrometer may comprise one or more ion traps or one or more ion trapping regions.

The spectrometer may comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

The spectrometer may comprise one or more energy analysers or electrostatic energy analysers.

The spectrometer may comprise one or more ion detectors.

The spectrometer may comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The spectrometer may comprise a device or ion gate for pulsing ions; and/or a device for converting a substantially continuous ion beam into a pulsed ion beam.

The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The spectrometer may comprise a chromatography or other separation device upstream of an ion source. The chromatography separation device may comprise a liquid chromatography or gas chromatography device. Alternatively, the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

A chromatography detector may be provided, wherein the chromatography detector comprises either:

a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or a non-destructive chromatography detector optionally selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

BRIEF DESCRIPTION OF THE DRAWINGS

Various embodiments will now be described, by way of example only, and with reference to the accompanying drawings in which.

DETAILED DESCRIPTION

The present disclosure may relate generally to methods of separating ions, for example according to their ion mobility, in which a separation device may comprise a region (e.g., the first region referred to herein) that may be arranged and adapted to switch between a trapping mode, in which ions are substantially trapped within the region, and a separation mode, in which ions are separated, for example according to their mass or ion mobility within the region.

The method may comprise (i) accumulating a first population of ions in a first region of a device, such as an ion mobility separator or mass separation device, (ii) separating said first population of ions according to their mass, mass to charge ratio or ion mobility in said device, and (iii) accumulating a second population of ions in said first region of said device whilst said first population of ions is being separated according to their mass, mass to charge ratio or ion mobility in said device. In various embodiments the device is an ion mobility separator, but may instead be a mass separation device such as a high pressure mass separation device.

This can provide better performance during separation since the population of ions to be separated are already contained within the ion mobility separator, and do not have to be transferred into it rapidly from e.g., an external ion trap. Ion heating and undesired fragmentation is avoided.

A known embodiment employing such an external ion trap will now be described with reference to FIG. 1.

Figure 1:
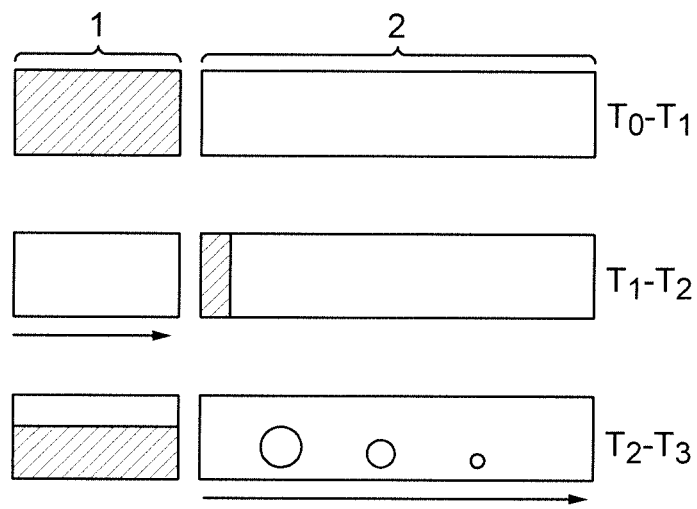
FIG. 1 shows a known arrangement in which an ion trap is positioned upstream of an ion mobility separator.

FIG. 1 shows an arrangement of an ion mobility spectrometer, wherein the ion mobility spectrometer may comprise an ion trap 1 and an ion mobility separator 2. As will be appreciated, FIG. 1 shows the location of a population of ions schematically at three consecutive points in time, $T_0$-$T_1$, $T_1$-$T_2$, and $T_2$-$T_3$.

The time period $T_0$-$T_1$ represents the time during a first ion mobility separation cycle, wherein during this time period the ion trap 1 may be filled with a first population of ions. During the time period $T_0$-$T_1$ a separate population of ions (not shown) may be separated within the ion mobility separator 2.

Over a subsequent time period $T_1$-$T_2$ the first population of ions may be driven or transferred from the ion trap 1 and into the ion mobility separator 2. During the time period $T_1$-$T_2$ there may be no driving force (e.g., a DC voltage or travelling wave) applied to the ion mobility separator 2 that would cause the first population of ions to separate according to their ion mobility.

During the time period $T_2$-$T_3$ a driving force (e.g., a DC voltage or travelling wave) may then be applied to ion mobility separator 2 so as to cause the first population of ions to be separated within the ion mobility separator 2 according to their ion mobility. During this period $T_2$-$T_3$ a second population of ions may be accumulated in ion trap 1.

In general the time period $T_0$-$T_1$ may be equal to the time period $T_2$-$T_3$, in order to maintain high duty cycle.

The time period $T_1$-$T_2$ is usually kept relatively short. This is to ensure that the populations of ions to be separated within the ion mobility separator 2 maintain a low spatial distribution in the direction of separation, and so that the ion trap 1 is rapidly available for the accumulation of the second (or subsequent) population of ions. During this period ions that may otherwise have entered ion trap 1 may be lost, which reduces the duty cycle of the ion mobility spectrometer.

The rapid ejection from the ion trap 1 into the ion mobility separator 2 typically requires a high driving force, which can lead to fragmentation and ion losses as discussed in the background section above.

Figure 2:
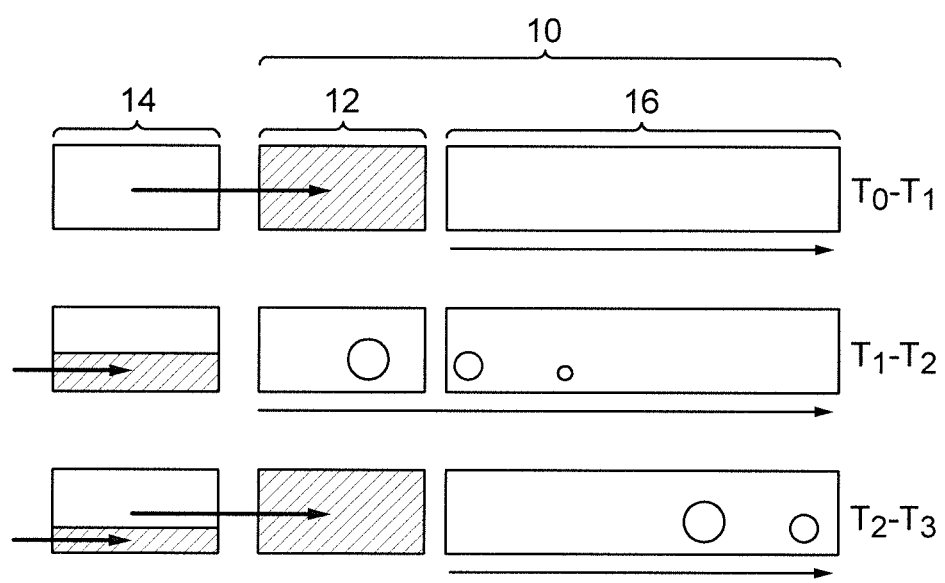
FIG. 2 shows an embodiment in accordance with the present disclosure wherein an accumulation and/or trapping region is provided within an ion mobility separator.

FIG. 2 shows an embodiment of the present disclosure, showing an ion mobility spectrometer or separation device comprising an ion mobility separator 10 and an upstream accumulation region 14. The ion mobility separator 10 comprises a plurality of regions 12, 16. The ion mobility separator 10 may not be limited to the regions shown, and more may be provided if necessary.

A first region 12 of the ion mobility separator 10 may be arranged and adapted to switch between an ion trapping or accumulating mode, in which ions are substantially trapped or accumulated within the first region 12, and an ion mobility separation mode, in which ions are separated according to their ion mobility within the first region 12.

The accumulation region 14 may be upstream of the first region 12 and may be arranged and adapted to trap or accumulate a population of ions in an ion trapping or accumulating mode, and then transfer ions from the accumulation region 14 into the ion mobility separator 10, specifically the first region 12 thereof, in an ion guiding mode, wherein ions are passed through and/or from the accumulation region 14 into the first region 12.

Ions may continuously enter the accumulation region 14 (e.g., from a continuous source of ions). The incoming ions may pass through the accumulation region 14 when it is operated in the ion guiding mode, and be stored in the accumulation region 14 when it is operated in the ion trapping mode.

A second region 16 may be downstream of the first region 12 (and the accumulation region 14) and may be arranged and adapted to receive ions from said first region 12 and separate them according to their ion mobility.

Thus, the arrangement shown in FIG. 2 comprises two trapping regions, namely the first region 12 and the accumulation region 14. The first region 12 is part of the ion mobility separator 10 and may operate in both a trapping mode and an ion mobility separation mode. The accumulation region 14 may be a separate ion trap. The first region 12 and the accumulation region 14 are followed by a second region 16, which is also part of the ion mobility separator 10 and may operate in an ion mobility separation mode.

During an ion mobility separation cycle, the ion mobility separation region may be defined as that part of the ion mobility separator that is causing ions to separate according to their ion mobility. As explained in more detail below, the second region 16 may always form part of the ion mobility separation region. The first region 12 may form part of the ion mobility separation region during a first part of the ion mobility separation cycle, and may then form a trapping region during a second part of the ion mobility separation cycle.

To illustrate this, and referring to FIG. 2, time period $T_0$-$T_1$ may represent a first time period of the ion mobility separation cycle. Ions may be transferred into the first region 12 (from accumulation region 14) and may accumulate within the first region 12 to form a first population of ions.

During the first time period $T_0$-$T_1$ the accumulation region 14 may act in an ion guiding mode, and ions (e.g., from a continuous beam of ions) may be urged through the accumulation region 14 and into the first region 12 of the ion mobility separator 10, for example using a DC voltage, or DC traveling wave. During this period the first region 12 may be in an ion trapping or accumulating mode, such that a first population of ions is accumulated in the first region 12.

During a second time period $T_1$-$T_2$ (e.g., at time $T_1$) the accumulation region 14 may switch from an ion guiding mode to an ion trapping or accumulating mode, and ions within and entering the accumulation region 14 may be prevented from entering the first region 12, such that a second population of ions may start to be accumulated in the accumulation region 14.

During the second time period $T_1$-$T_2$ (e.g., at time $T_1$) the first region 12 may be switched from an ion trapping or accumulating mode to an ion mobility separation mode. In the second time period $T_1$-$T_2$ the first population of ions that has been accumulated in the first region 12 may then be caused to separate according to their ion mobility within the first region 12 and second region 16, which may also be operating in an ion mobility separation mode. Thus, during the second time period $T_1$-$T_2$ the first region 12 and the second region 16 may form the ion mobility separation region.

A driving force, for example a DC voltage, or DC traveling wave may be applied to the first region 12 and the second region 16, which may cause the first population of ions to separate according to their ion mobility as they are driven through the ion mobility separation region.

At time $T_2$, prior to all ions in the first population of ions exiting the second region 16, but after all ions from the first ion population of ions have exited the first region 12, the first region 12 may be switched from an ion mobility separation mode to an ion trapping or accumulating mode. For example, the driving force may be removed from the first region 12. At this point only the second region 16 may form the ion mobility separation region.

During a third time period $T_2$-$T_3$, the accumulation region 14 may be switched from an ion trapping or accumulating mode to an ion guiding mode. During the third time period the second population of ions (which has accumulated within the accumulation region 14 during time period $T_1$-$T_2$) is transferred and accumulated within the first region 12.

Ions entering and passing through the accumulation region 14 during time period $T_2$-$T_3$, may also be transferred into and accumulate within the first region 12 to add to the second population of ions.

At the end of the third time period $T_2$-$T_3$ the second population of ions has been accumulated in the first region 12. At this point the conditions of the second time period ($T_1$-$T_2$) can be repeated, in which the accumulation region 14 switches from an ion guiding mode to an ion trapping or accumulating mode, and the first region 12 switches from an ion trapping or accumulating mode to an ion mobility separation mode.

As such, the second population of ions can be separated according to their ion mobility in the first region 12 and the second region 16 in a similar manner to the first population of ions during time period $T_1$-$T_2$. The first population of ions may not have fully exited the second region 16, but the time periods may be chosen to avoid any overlap of the first and second populations of ions. At this point a third population of ions can be accumulated in the accumulation region 14, until the second population of ions have been driven from the first region 12 and the process can repeat for the third and further populations of ions.

The first region 12 may be significantly shorter in length compared to the second region 16, in which case the second time period $T_1$-$T_2$ may be a small percentage of the ion mobility separation cycle (in this case $T_1$-$T_3$). As such, transfer of the population of ions from the accumulation region 14 to the first region 12 (during the second time period $T_2$-$T_3$) can occur over a relatively long period of time compared to the rapid ion transfer in the prior art. This can avoid ion heating and ion losses associated with the prior art.

It will be appreciated that using the above method successive populations of ions can be separated according to their ion mobility. It will also be appreciated that the disclosed arrangement can lead to a duty cycle of 100%, since a beam of ions can be continuously passed into the upstream accumulation region, which either accumulates the ions (e.g., during time period $T_1$-$T_2$) or passes them through to the first region 12 (e.g., during time period $T_2$-$T_3$). This can mean that no ions from the incoming beam of ions are lost to the system or otherwise.

It will also be appreciated that the disclosed arrangement can avoid a fast transfer of ions from an external ion trap into an ion mobility separator, which has been found to lead to ion heating and undesired fragmentation. That is, the transfer of ions from the upstream accumulation region 14 into the first region 12 may be relatively slow, since the first region 12 may act in both a trapping mode and an ion mobility separation mode. This is in contrast to conventional arrangements in which the transfer of ions from an upstream ion trap into an ion mobility separator must be relatively quick, to avoid substantial dispersion of the ions in the ion mobility separator.

In accordance with the disclosure, a subsequent population of ions may be accumulated in the upstream trapping region (or accumulation region 14) whilst the preceding population of ions are separated according to their ion mobility in the downstream trapping/separation region (or first region 12).

Once the preceding population of ions has exited the downstream trapping/separation region (or first region 12), but before the preceding population of ions has exited the ion mobility separator 10 (e.g., whilst the preceding population of ions is in the second region 16), the subsequent population of ions can be transferred to the downstream trapping/separation region (or first region 12). The subsequent population of ions may include ions that enter and are passed through the accumulation region 14 during the transfer.

After the preceding population of ions has left the ion mobility separator 10 (or once the subsequent population of ions has filled the downstream trapping/separation region) the subsequent population of ions becomes the preceding population of ions and may be separated according to their ion mobility in the downstream trapping/separation region.

A (new) subsequent population of ions may be accumulated in the upstream trapping region (or accumulation region 14) whilst the preceding population of ions are separated according to their ion mobility in the downstream trapping/separation region (or first region 12), and this process may repeat for successive populations of ions.

Figure 3:
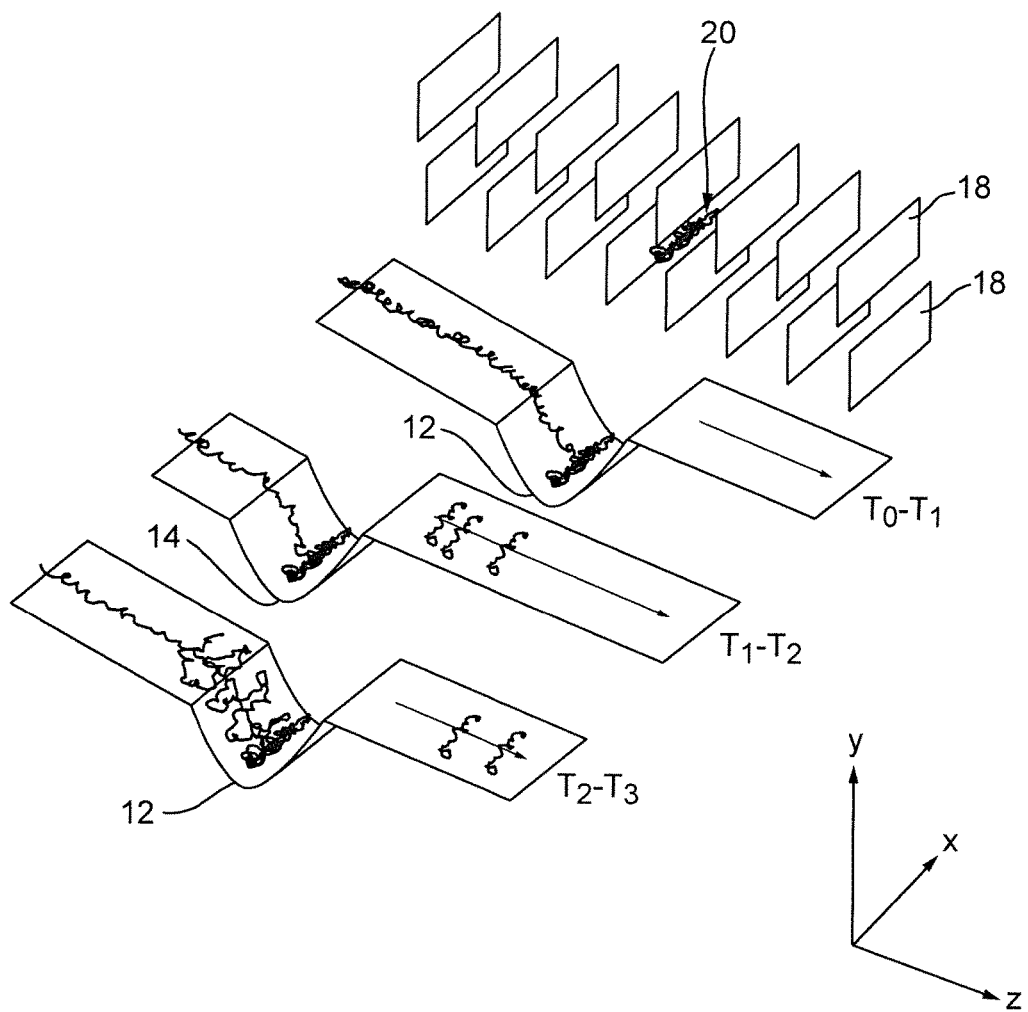
FIG. 3 shows an embodiment wherein an ion mobility separator comprises a plurality of electrodes stacked adjacent to one another.

FIG. 3 shows schematically an ion mobility separator 10 in accordance with the present disclosure.

The ion mobility separator 10 may comprise a plurality of electrode pairs 18. The electrode pairs 18 may be stacked adjacent to one another, and alternate phases of an AC or RF voltage may be applied to adjacent pairs of electrodes 18 in order to confine ions radially within the ion mobility separator 10 in the y direction. Each of the pairs of electrodes 18 may comprise a first plate electrode located opposite a second plate electrode, and in use ions may travel through the gap between the first and second plate electrodes.

The successive pairs of electrodes 18 may form a first array of first electrodes located opposite a second array of second electrodes. The first electrodes and/or the second electrodes may form plate, planar or mesh electrodes. The plane of the first and/or second electrodes may be oriented in the y direction as shown in FIG. 3, or the z or x direction (or any other direction suitable to confine ions within the gap between the first and second electrodes).

As discussed above a population of ions 20 may be confined in the y direction by application of an AC or RF voltage to the pairs of electrodes 18, wherein opposite phases of the AC or RF voltage may be applied to adjacent pairs of electrodes 18.

Ion confinement in the x direction may be accomplished by creating a DC confining field in the x direction. The DC confinement can be accomplished by providing separate DC electrodes (not shown), for example intermediate plate, planer or mesh electrodes that run longitudinally along the length of the ion mobility separator 10, and between the first array of first electrodes and the second array of second electrodes.

In an alternative embodiment, the ion mobility separator may comprise a plurality of electrodes, wherein each electrode has an aperture through which ions travel in use. In such an embodiment, alternate phases of an AC or RF voltage may be applied to adjacent electrodes to confine ions radially within the ion mobility separator.

The population of ions 20 may be confined in the z direction (longitudinally) by application of appropriate DC potential to adjacent pairs of electrodes 18. For example, a potential well may be created by applying appropriate DC potentials to the successive pairs of electrodes 18. For example, an electrode pair may be held at a relatively low DC potential compared to the electrode pairs either side of it. This can create a DC potential well that confines ions within the well in the z direction.

FIG. 3 shows schematically the position of a population of ions in the first region 12 and the accumulation region 14 over the time from $T_0$-$T_3$ as described in relation to FIG. 2.

In the first time period $T_0$-$T_1$, it can be seen that the ion population in the first region 12 has a small spatial spread in the z direction compared to the spatial spread in the x direction. As the first region 12 may form part of the ion mobility separation region of the ion mobility separator (e.g., during the second time period $T_1$-$T_2$), it can be advantageous that, prior to the first region 12 switching suddenly from an ion trapping mode to an ion mobility separation mode, ions are focused within the first region 12 with a small spatial spread in the direction of ion mobility separation (i.e., the z direction). This can ensure maximum ion mobility resolution without requiring additional compression of the ion cloud in this direction, since the ions that are to be separated according to their mobility have a very similar starting point.

Furthermore, ions may be allowed to have a larger spatial spread in a direction orthogonal to the direction of ion mobility separation (i.e., the x direction). This can maximise the space charge capacity of the first region 12, which can switch suddenly from a trapping region to an ion mobility separation region, as well as the downstream ion mobility separation region (i.e., the second region 16).

Ions may be driven or transferred between the first region 12 and/or the accumulation region 14 and/or the second region 16 using static DC fields, DC potentials or travelling DC waves, any combination of these driving methods, or any other suitable driving method.

The accumulation region 14 may be extended in the z direction and/or the x direction. As the time scale over which ions are transferred from the accumulation region 14 to the first region 12 (e.g., the time period $T_2$-$T_3$) is extended using the method described herein, ions may still be transferred with minimal losses even if the accumulation region 14 has a relatively large extent in the z direction.

Both trapping regions (i.e., first region 12 and accumulation region 14) may be extended in either or both the x and y directions. In the ion mobility separator 10, and in particular when applying a transient DC potential to successive pairs of electrodes in order to urge or (i.e., a travelling wave), the distance between the confining pairs of electrodes 18 in either the x or y direction may be limited, such that sufficient driving force is experienced by ions without having to apply an excessively large transient DC potential.

The first region 12 and/or the accumulation region 14 and/or the ion mobility separator 10 may be extended in this manner to form an annular volume to maximize space charge capacity.

From the above discussion it will be appreciated that accumulating a subsequent population of ions within the first region 12 whilst the preceding population of ions are being separated according to their ion mobility within the ion mobility separator 10 can achieve better resolution and performance compared to conventional methods, for example those that transfer ions into an ion mobility separator from an external ion trap.

Various embodiments are contemplated and defined herein that improve methods of ion mobility spectrometry. For example, ensuring that the ion population in the first region 12 has a relatively small spatial spread in the direction of ion mobility separation, and a relatively large spatial spread in the direction orthogonal to ion mobility separation, can achieve improved resolution and performance as discussed above.

Using two trapping regions (i.e. the first region 12 and the accumulation region 14) as described herein can eliminate the requirement for rapid ion transfer from a separate ion trapping region to an ion mobility separation region whilst maintaining high duty cycle. Extending the ion transfer time using two trapping regions as discussed herein may reduce ion losses and unwanted ion fragmentation.

The ion mobility separator referred to herein (such as ion mobility separator 10) may be part of a larger device, such as a mass or ion mobility spectrometer, or a hybrid ion mobility-mass spectrometry (IMS-MS) or mass spectrometry-ion mobility (MS-IMS) device. All regions of (or the entirety of) the ion mobility separator may be arranged and adapted to separate ions according to their ion mobility, for example in at least one mode of operation. Using such a definition, the accumulation region 14 would not form part of the ion mobility separator 10, even if it formed part of the same physical device, for example a stack of electrodes. All regions of (or the entirety of) the ion mobility separator may be operated at the same or substantially the same pressure. All regions of (or the entirety of) the ion mobility separator may contain the same buffer gas.

Various embodiments are contemplated in which the arrangement of first, second and second regions may be applied to any type of ion separation, for example mass or mass to charge ratio. For example the ion mobility separator 10 may instead be a mass separation device, for example a high-pressure mass separation device. The features described above in relation to the ion mobility separator, for example the arrangement of first, second and second regions and/or the electrodes and/or the voltages applied thereto, may also be features of the mass separation device. The method features relating to the first, second and second regions may be applied mutatis mutandis to a mass separation device comprising these regions and arranged in the same manner as the ion mobility separator described above. For example, in such embodiments the first region may be arranged and adapted to switch between a trapping mode, in which ions are substantially trapped within the first region, and a separation mode, in which ions are separated according to a different physico-chemical property, for example mass or mass to charge ratio, within the first region.

Although the present invention has been described with reference to preferred embodiments, it will be understood by those skilled in the art that various changes in form and detail may be made without departing from the scope of the invention as set forth in the accompanying claims.

The invention claimed is:

1. A method of separating ions according to their ion mobility, comprising:
   (i) accumulating a first population of ions in a first region of an ion mobility separator;
   (ii) separating said first population of ions according to their ion mobility in said first region of said ion mobility separator and in a second region of said ion mobility separator; and
   (iii) accumulating a second population of ions in said first region of said ion mobility separator after said first population of ions have exited the first region, and whilst said first population of ions are being separated according to their ion mobility in said second region of said ion mobility separator,
   wherein step (ii) comprises accumulating said second population of ions in an ion trap upstream of said first region, whilst said first population of ions are being separated according to their ion mobility in said first region of said ion mobility separator, wherein said ion trap is external to said ion mobility separator,
   wherein said first region of said ion mobility separator switches between a trapping mode in steps (i) and (iii), in which ions are substantially trapped within said first region and not separated according to their ion mobility, and an ion mobility separation mode in step (ii), in which ions are separated according to their ion mobility within said first region.

2. A method as claimed in claim 1, wherein step (iii) comprises transferring said second population of ions from said upstream ion trap and into said first region, and continuing to pass ions through said upstream ion trap and into said first region so as to accumulate said second population of ions in said first region.

3. A method as claimed in claim 1, wherein said ion mobility separator comprises a second region downstream of said first region, and step (ii) comprises separating said first population of ions according to their ion mobility in said first and second regions of said ion mobility separator.

4. A method as claimed in claim 3, wherein step (iii) comprises accumulating said second population of ions in said first region of said ion mobility separator whilst said first population of ions are being separated according to their ion mobility in said second region of said ion mobility separator.

5. A method as claimed in claim 1, wherein step (iii) comprises accumulating said second population of ions in said first region of said ion mobility separator after said first population of ions have exited said first region of said ion mobility separator.

6. A method as claimed in claim 1, further comprising:
   (iv) separating said second population of ions according to their ion mobility in said ion mobility separator; and
   (v) accumulating a third population of ions in said first region of said ion mobility separator whilst said second population of ions are being separated according to their ion mobility.

7. A method as claimed in claim 6, further comprising:
   repeating steps (ii) to (v) for said third and further populations of ions, such that subsequent populations of ions are accumulated in said first region of said ion mobility separator whilst preceding populations of ions are being separated according to their ion mobility.

8. A method as claimed in claim 1, further comprising directing a beam of ions continuously into the upstream ion trap.

9. A method as claimed in claim 1, wherein said ion mobility separator comprises an RF-confined ion mobility separator.

10. A method as claimed in claim 9, wherein said ion mobility separator comprises a plurality of electrodes stacked adjacent to one another, wherein alternate phases of an RF voltage are applied to adjacent electrodes.

11. A method as claimed in claim 10, wherein each of said plurality of electrodes comprise apertures through which ions travel in use.

12. A method as claimed in claim 10, wherein said plurality of electrodes comprises a plurality of pairs of electrodes stacked adjacent to one another, wherein alternate phases of an RF voltage are applied to adjacent pairs of electrodes.

13. A method as claimed in claim 12, wherein each of said pair of electrodes comprises a first plate electrode opposite a second plate electrode, wherein in use ions travel through the gap between said first and second plate electrodes.

14. A method as claimed in claim 1, wherein said first region ion trap comprise RF-confined regions.

15. A method as claimed in claim 1, wherein said ion trap of said ion mobility separator is arranged and adapted to trap or accumulate a population of ions and then transfer the population of ions from the ion trap into the first region.

16. A method as claimed in claim 1, wherein step (i) comprises accumulating said first population of ions in said first region such that within the first region the first population of ions has a relatively small spatial spread in the direction of ion mobility separation, and a relatively large spatial spread in the direction orthogonal to ion mobility separation.

17. An ion mobility spectrometer or separation device comprising:
   an ion mobility separator comprising a first region arranged and adapted to accumulate consecutive populations of ions; and
   a control system arranged and adapted:
   (i) to accumulate a first population of ions in said first region of said ion mobility separator;
   (ii) to separate said first population of ions according to their ion mobility in said first region of said ion mobility separator and in a second region of said ion mobility separator; and
   (iii) to accumulate a second population of ions in said first region of said ion mobility separator after said first population of ions have exited the first region, and whilst said first population of ions are being separated according to their ion mobility in said second region of said ion mobility separator,
   wherein step (ii) comprises accumulating said second population of ions in an ion trap upstream of said first region, whilst said first population of ions are being separated according to their ion mobility in said first region of said ion mobility separator, wherein said ion trap is external to said ion mobility separator,
   wherein said first region of said ion mobility separator switches between a trapping mode in steps (i) and (iii), in which ions are substantially trapped within said first region and not separated according to their ion mobility, and an ion mobility separation mode in step (ii), in which ions are separated according to their ion mobility within said first region.

18. An ion mobility spectrometer or separation device as claimed in claim 17, further comprising an ion trap upstream of said first region, wherein said control system is arranged and adapted:
   to accumulate said second population of ions in said ion trap whilst said first population of ions are being separated according to their ion mobility in said first region of said ion mobility separator.

19. A method of separating ions in a device, wherein the device comprises a first region, an ion trap upstream of the first region and a second region downstream of the first region, wherein the first and second regions form part of an ion mobility separator and said ion trap is external to said ion mobility separator, wherein the method comprises the steps of:
   (i) driving a first population of ions through the first and second regions so as to separate a first population of ions, whilst accumulating a second population of ions in the ion trap;
   (ii) after the first population of ions has exited the first region, but prior to the first population of ions exiting the second region, transferring the second population of ions into the first region and trapping the second population of ions within the first region; and then
   (iii) driving the second population of ions through the first and second regions so as to separate the second population of ions, whilst accumulating a third population of ions in the ion trap;
   (iv) repeating steps (ii) and (iii) for the third and further populations of ions so as to successively separate the third and further populations of ions,
   wherein said first region switches between a trapping mode in step (ii), in which ions are substantially trapped within said first region and not separated according to their ion mobility, and an ion mobility separation mode in steps (i) and (iii), in which ions are separated according to their ion mobility within said first region.

20. An apparatus comprising a device for separating ions and a control system, wherein the device comprises a first region, an ion trap upstream of the first region and a second region downstream of the first region,
   wherein the first and second regions form part of an ion mobility separator and said ion trap is external to said ion mobility separator, wherein the control system is arranged and adapted:
   (i) to drive a first population of ions through the first and second regions so as to separate the first population of ions, for example according to their ion mobility, whilst accumulating a second population of ions in the ion trap;
   (ii) after the first population of ions has exited the first region, but prior to the first population of ions exiting the second region, to transfer the second population of ions into the first region and trap the second population of ions within the first region; and then
   (iii) to drive the second population of ions through the first and second regions so as to separate the second population of ions, for example according to their ion mobility, whilst accumulating a third population of ions in the ion trap; and
   (iv) to repeat steps (ii) and (iii) for the third and further populations of ions so as to successively separate the third and further populations of ions, for example according to their ion mobility,
   wherein said first region of said ion mobility separator switches between a trapping mode in step (ii), in which ions are substantially trapped within said first region and not separated according to their ion mobility, and an ion mobility separation mode in steps (i) and (iii), in which ions are separated according to their ion mobility within said first region.

* * * * *